United States Patent
Goebel et al.

(10) Patent No.: US 7,749,526 B2
(45) Date of Patent: Jul. 6, 2010

(54) VERMIN-REPELLANT COMPOSITIONS AND COMPOUNDS

(75) Inventors: Thomas Goebel, Lörrach (DE); Tania Cavaliero, Neuchatel (CH); Jacques Bouvier, Neuchâtel (CH)

(73) Assignee: Novartis AG, Basel (CH)

( * ) Notice: Subject to any disclaimer, the term of this patent is extended or adjusted under 35 U.S.C. 154(b) by 1102 days.

(21) Appl. No.: 10/537,871

(22) PCT Filed: Dec. 16, 2003

(86) PCT No.: PCT/EP03/14336

§ 371 (c)(1),
(2), (4) Date: Jul. 27, 2005

(87) PCT Pub. No.: WO2004/054964

PCT Pub. Date: Jul. 1, 2004

(65) Prior Publication Data

US 2006/0140996 A1    Jun. 29, 2006

(30) Foreign Application Priority Data

Dec. 17, 2002 (EP) .................................. 02028328

(51) Int. Cl.
- *A01N 25/00* (2006.01)
- *A01N 37/18* (2006.01)
- *A01N 33/02* (2006.01)
- *A01N 33/18* (2006.01)
- *A01N 33/24* (2006.01)
- *A01N 31/14* (2006.01)
- *C07C 233/00* (2006.01)

(52) U.S. Cl. ........................ 424/405; 514/629; 514/663; 514/672; 514/716; 514/722; 514/740; 514/875; 514/876; 514/919; 564/215

(58) Field of Classification Search .................. 424/405
See application file for complete search history.

(56) References Cited

U.S. PATENT DOCUMENTS

| | | | | |
|---|---|---|---|---|
| 3,309,333 A | * | 3/1967 | Mod et al. .................. | 524/220 |
| 3,515,754 A | | 6/1970 | Mod et al. | |
| 3,519,661 A | * | 7/1970 | Mod et al. .................... | 554/63 |
| 3,538,123 A | * | 11/1970 | Mod et al. .................. | 549/553 |
| 3,584,030 A | * | 6/1971 | Mod et al. .................. | 560/123 |
| 3,712,926 A | | 1/1973 | Peterson | |

FOREIGN PATENT DOCUMENTS

DE    44 35 114        4/1995
JP    48-042279 B    * 12/1973

OTHER PUBLICATIONS

Database WPI Section Ch. Week 199036 Serwent Publication Ltd. London, GB Class E16, AN1990-273296 XP002241616 & SU 1 525 148.

D.A. Konen et al, "Specific and Selective Site Reactions in Alkanoate Derivatives. 1. Factors Affecting Omega-1 Chlorinations by N-Chloroamines" Journal of Organic Chemistry, Bd. 44, Nr. 20 pp. 3594-3596, (1979).

* cited by examiner

*Primary Examiner*—Johann R Richter
*Assistant Examiner*—Nathan W Schlientz

(57) ABSTRACT

Compounds of formula (I) are described for deterring vermin, wherein R is unbranched or branched $C_1$-$C_{15}$ alkyl, which is unsubstituted or substituted by halogen, cyano or nitro; R1 and R2 are unbranched or branched $C_1$-$C_{12}$ alkyl, preferably $C_1$-$C_6$ alkyl, which is unsubstituted or substituted by halogen, cyano or nitro; and X and Y, independently of one another, are a straightchain or branched alkylene bridge with 1 to 20 carbon atoms, preferably an alkylene bridge with 1 to 3 carbon atoms, which is unsubstituted or substituted by halogen, cyano or nitro. Furthermore, an essentially non-therapeutical process for deterring vermin is described, which is based on the usage of these compounds, as well as verminrepellent compositions containing these compounds as the active ingredient, and finally the use of these compounds for producing vermin-deterring compositions and their usage in deterring vermin from animals, humans and objects. New compounds within the scope of formula (I) are also described.

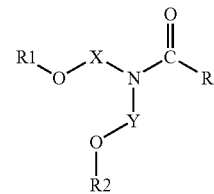

(I)

15 Claims, No Drawings

VERMIN-REPELLANT COMPOSITIONS AND COMPOUNDS

This application is a National Phase Application under §371 of International Application Number PCT/EP2003/014336 filed on Dec. 16, 2003.

The present invention relates to the novel compounds named under formula (I), the novel representatives thereof within the scope of formula (I), and an essentially non-therapeutical process for repelling vermin which is based on the usage of these compounds. Furthermore, it relates to corresponding vermin-repellent compositions which contain these substances as the active ingredient, to compounds of formula (I) for the preparation of vermin-deterring compositions, and to the use of compounds of formula (I) in the defence against vermin.

The substances under discussion are compounds of formula (I)

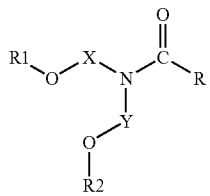

wherein

R is unbranched or branched $C_1$-$C_{15}$-alkyl, preferably branched $C_1$-$C_9$-alkyl, which is unsubstituted or is substituted by halogen, cyano or nitro;

R1 and R2 are unbranched or branched $C_1$-$C_{12}$-alkyl, preferably $C_1$-$C_6$-alkyl, which is unsubstituted or is substituted by halogen, cyano or nitro; and X and Y, independently of one another, form a straight-chain or branched alkylene bridge with 1 to 20 carbon atoms, preferably an alkylene bridge with 1 to 3 carbon atoms, which is unsubstituted or substituted by halogen, cyano or nitro.

One preferred subgroup is formed by those compounds within the scope of formula (I), in which R is $CH(C_1$-$C_4$ alkyl$)_2$, whereby the two $C_1$-$C_4$ alkyl-radicals are of a different or the same length and are branched or preferably unbranched.

Compounds of formula (I), wherein R1 and R2 are defined as under formula (I) and R is $CH(C_2$-$C_4$ alkyl$)_2$, whereby the two $C_2$-$C_6$ alkyl radicals are identical and branched or preferably unbranched, are new compounds and represent a preferred object of the present invention.

Another preferred group within the scope of the compounds of formula (I) consists of those compounds in which X and Y, independently of one another, are methylene or ethylene.

Another preferred group within the scope of the compounds of formula (I) consists of those compounds in which R1 and R2, independently of one another, are methyl or ethyl.

A further preferred group within the scope of the compounds of formula (I) consists of those compounds in which R is $CH(C_3H_7$-n$)_2$.

Certain compounds of this type of structure are known from literature, but for a completely different application.

For example, substances are described in U.S. Pat. No. 3,515,754, which preferably bear a long-chained fatty acid radical as the group R—C(O)— [see formula (I)], the only exception being N,N-bis(2-ethoxyethyl)-2-ethylhexanamide from example 4. Said substances serve as plasticisers.

In U.S. Pat. No. 3,712,926, the production of a few representatives of formula (I), e.g. $CH_3$—CO—$N(CH_2OCH_3)_2$ is likewise described. These serve as so-called crosslinkers for coatings of surfaces.

In Derwent Publication no. XP002241615, the production of chlorinated N,N-bis(2-ethoxyethyl)dodecanamide, which is used in photosensitive layers, is described.

In German published specification DE 44 35 114, insecticidal and insect-deterring compositions are described, the compounds of the structure type

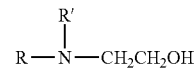

wherein R is H, $CH_2CH_2OH$ or R''' and R' is H or $CH_2CH_2OH$ and R''' is a fatty acid radical derived from coconut oil.

It has surprisingly been found that the compounds of formula (I) are eminently suitable for deterring vermin. Through the usage according to the invention of the above compounds, a great variety of vermin of humans, animals, objects or specific places can be deterred, whereby numerous compounds within the scope of formula (I) are notable for their particularly long duration of efficacy.

The alkyl groups present in the definitions of the substituents may be straight-chained or preferably branched, depending on the number of carbon atoms, and they may be for example methyl, ethyl, propyl, butyl, pentyl, hexyl, heptyl, octyl, nonyl, decyl, undecyl, dodecyl, tetradecyl, hexadecyl, octadecyl or eicosyl, as well as preferably the branched isomers thereof, for example isopropyl, isobutyl, sec.-butyl, tert.-butyl, isopentyl, neopentyl or isohexyl, etc. Within the context of the invention, preference is given to the compounds of formula (I), wherein R is —$CH(CH_3)CH_3$, —$CH(CH_3)CH_2CH_3$, —$CH(CH_3)(CH_2)_2CH_3$, —$CH(CH_3)(CH_2)_3CH_3$, —$CH(CH_3)(CH_2)_4CH_3$, —$CH(CH_3)(CH_2)_5CH_3$, —$CH(CH_3)(CH_2)_8CH_3$, —$CH(CH_3)(CH_2)_7CH_3$, —$CH(CH_3)(CH_2)_8CH_3$, —$CH(CH_3)(CH_2)_9CH_3$, —$CH(CH_3)(CH_2)_{10}CH_3$, —$CH(CH_3)(CH_2)_{11}CH_3$, —$CH(CH_3)(CH_2)_{12}CH_3$, —$CH(CH_2CH_3)CH_2CH_3$, —$CH(CH_2CH_3)(CH_2)_2CH_3$, —$CH(CH_2CH_3)(CH_2)_3CH_3$, —$CH(CH_2CH_3)(CH_2)_4CH_3$, —$CH(CH_2CH_3)(CH_2)_5CH_3$, —$CH(CH_2CH_3)(CH_2)_6CH_3$, —$CH(CH_2CH_3)(CH_2)_7CH_3$, —$CH(CH_2CH_3)(CH_2)_8CH_3$, —$CH(CH_2CH_3)(CH_2)_9CH_3$, —$CH(CH_2CH_3)(CH_2)_{10}CH_3$, —$CH(CH_2CH_3)(CH_2)_{11}CH_3$, —$CH(CH_2CH_2CH_3)CH_2CH_3$, $CH(CH_2CH_2CH_3)(CH_2)_2CH_3$, $CH(CH_2CH_2CH_3)(CH_2)_3CH_3$, $CH(CH_2CH_2CH_3)(CH_2)_4CH_3$, $CH(CH_2CH_2CH_3)(CH_2)_5CH_3$, $CH(CH_2CH_2CH_3)(CH_2)_6CH_3$, $CH(CH_2CH_2CH_3)(CH_2)_7CH_3$, $CH(CH_2CH_2CH_3)(CH_2)_8CH_3$, $CH(CH_2CH_2CH_3)(CH_2)_9CH_3$, $CH(CH_2CH_2CH_3)(CH_2)_{10}CH_3$, $CH(CH_2CH_2CH_2CH_3)CH_2CH_3$, $CH(CH_2CH_2CH_2CH_3)(CH_2)_2CH_3$, $CH(CH_2CH_2CH_2CH_3)(CH_2)_3CH_3$, $CH(CH_2CH_2CH_2CH_3)(CH_2)_4CH_3$, $CH(CH_2CH_2CH_2CH_3)(CH_2)_5CH_3$, $CH(CH_2CH_2CH_2CH_3)(CH_2)_6CH_3$, $CH(CH_2CH_2CH_2CH_3)(CH_2)_7CH_3$, $CH(CH_2CH_2CH_2CH_3)(CH_2)_8CH_3$, $CH(CH_2CH_2CH_2CH_3)(CH_2)_9CH_3$, $CH(CH_2CH_2CH_2CH_2CH_3)CH_2CH_3$, $CH(CH_2CH_2CH_2CH_2CH_3)(CH_2)_2CH_3$, $CH(CH_2CH_2CH_2CH_2CH_3)(CH_2)_3CH_3$, $CH(CH_2CH_2CH_2CH_2CH_3)(CH_2)_4CH_3$, $CH(CH_2CH_2CH_2CH_2CH_3)(CH_2)_5CH_3$, $CH(CH_2CH_2CH_2CH_2CH_3)(CH_2)_6CH_3$, CH(CH₂CH₂CH₂CH₂CH₃)(CH₂)₇CH₃,
CH(CH₂CH₂CH₂CH₂CH₂CH₃)CH₂CH₃,
CH(CH₂CH₂CH₂CH₂CH₂CH₃)(CH₂)₂CH₃,
CH(CH₂CH₂CH₂CH₂CH₂CH₃)(CH₂)₃CH₃,
CH(CH₂CH₂CH₂CH₂CH₂CH₃)(CH₂)₄CH₃,
CH(CH₂CH₂CH₂CH₂CH₂CH₃)(CH₂)₅CH₃,
CH(CH₂CH₂CH₂CH₂CH₂CH₃)(CH₂)₆CH₃,
CH(CH₂CH₂CH₂CH₂CH₂CH₃)(CH₂)₇CH₃,
CH(CH₂CH₂CH₂CH₂CH₂CH₂CH₃)CH₂CH₃,
CH(CH₂CH₂CH₂CH₂CH₂CH₂CH₃)(CH₂)₂CH₃,
CH(CH₂CH₂CH₂CH₂CH₂CH₂CH₃)(CH₂)₃CH₃,
CH(CH₂CH₂CH₂CH₂CH₂CH₂CH₃)(CH₂)₄CH₃,
CH(CH₂CH₂CH₂CH₂CH₂CH₂CH₃)(CH₂)₅CH₃,
CH(CH₂CH₂CH₂CH₂CH₂CH₂CH₃)(CH₂)₆CH₃,
CH(CH₂CH₂CH₂CH₂CH₂CH₂CH₂CH₃)CH₂CH₃,
CH(CH₂CH₂CH₂CH₂CH₂CH₂CH₂CH₃)(CH₂)₂CH₃,
CH(CH₂CH₂CH₂CH₂CH₂CH₂CH₂CH₃)(CH₂)₃CH₃,
CH(CH₂CH₂CH₂CH₂CH₂CH₂CH₂CH₃)(CH₂)₄CH₃, and
CH(CH₂CH₂CH₂CH₂CH₂CH₂CH₂CH₃)(CH₂)₅CH₃. Of these, the groups that are most preferred are those in which the CH-group is symmetrically substituted. CH(CH₂CH₂CH₃)(CH₂)₂CH₃ is preferred in particular.

Halogen normally signifies fluorine, chlorine, bromine or iodine, preferably fluorine or chlorine, especially chlorine, whereby the corresponding alkyl substituent may contain one or more identical or different halogen atoms. Non-limiting examples of halogenated alkyl substituents are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers, mono- to nonasubstituted by fluorine, chlorine and/or bromine, such as $CF(CF_3)CHFCF_3$ or $CH_2(CF_2)_2CF_3$.

A preferred sub-group in the context of formula (I) is formed by compounds wherein R is branched $C_1$-$C_{12}$ alkyl, preferably $C_4$-$C_9$ alkyl Particular preference is given to compounds of formula (I), wherein the substituent R is unsubstituted.

In the context of the present invention, preference is given to compounds in which X and Y, independently of one another, form a straight-chain or branched alkylene bridge with 1 to 3 carbon atoms, which is unsubstituted. Ethylene is preferred in particular.

Notable compounds are those of formula (I), in which R1 and R2 are unbranched $C_1$-$C_6$ alkyl, preferably methyl or ethyl.

One especially preferred representative of the compounds of formula (I) is 2-propyl-pentanoic acid-bis-(2-methoxyethyl)-amide, which has the following structural formula:

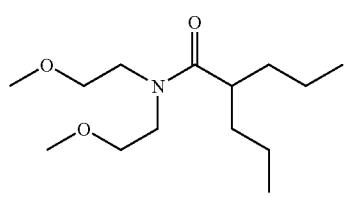

The production of the compounds of formula (I) leads to its free form or to the salt form.

Production of the compounds of formula (I) is accomplished, for example, whereby a compound of formula

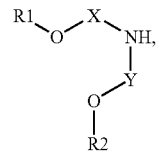

which is known or may be produced analogously to corresponding known compounds, and wherein $R_1$, $R_2$, X, Y are defined as given for formula (I), is reacted with a compound of formula

which is likewise known or may be prepared analogously to corresponding known compounds, and wherein R is defined as given for formula (I) and Q is a leaving group, optionally in the presence of a basic catalyst, and if desired, a compound of formula (I) obtainable according to the method or in another way, respectively in free form or in salt form, is converted into another compound of formula (I), a mixture of isomers obtainable according to the method is separated by known methods and the desired isomer isolated and/or a free compound of formula (I) obtainable according to the method is converted into a salt or a salt of a compound of formula (I) obtainable according to the method is converted into the free compound of formula (I) or into another salt.

What has been stated above for salts of compounds I also applies analogously to salts of the starting materials listed hereinabove and hereinbelow.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide.

Preferred leaving groups Q are halogens, tosylates, mesylates and triflates, most preferably halogens, especially chlorine.

Suitable bases for facilitating the reaction are e.g. alkali metal or alkaline earth metal hydroxides, hydrides, amides, alkanolates, acetates, carbonates, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Preference is given to diisopropylethylamine and 4-(N,N-dimethylamino) pyridine. The reaction advantageously takes place in a temperature range of ca. 0° C. to ca. 100° C., preferably from ca. 10° C. to ca. 40° C.

The compounds of formula I are colourless to pale yellow, neutral-tasting oils, which are relatively readily volatile. Kinetic investigations show that they do not penetrate into the skin after topical application. It is not possible to establish measurable blood levels of the compounds of formula (I), nor conceivable degradation products. Consequently, topical application is not a therapeutical procedure for animals or humans.

In the context of the present invention, vermin are understood to be in particular insects, mites and ticks. These include insects of the order *Lepidoptera, Coleoptera, Homoptera, Heteroptera, Diptera, Thysanoptera, Orthoptera, Anoplura, Siphonaptera, Mallophaga, Thysanura, Isoptera, Psocoptera* and *Hymenoptera*. However, the vermin which may be mentioned in particular are those which trouble humans or animals and carry pathogens, for example flies such as *Musca domestics, Musca vetustissima, Musca autumnalis, Fannia canicularis, Sarcophaga camaria, Lucilia cuprina, Hypoderna bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (*Nematocera*), such as *Culicidae, Simuliidae, Psychodidae*, but also blood-sucking vermin, for example fleas, such as *Ctenocephalides felis* and *Ctenocephalides canis* (cat and dog fleas), *Xenopsylla cheopis, Pulex initans, Dermatophilus penetrans*, lice, such as *Damalina ovis, Pediculus humanis*, biting flies and horse-flies (*Tabanidae*), *Haematopota* spp. such as *Haematopota pluvialis, Tabanidea* spp. such as *Tabanus nigrovittatus, Chrysopsinae* spp. such as *Chrysops caecutiens*, tsetse flies, such as species of *Glossinia*, biting insects, particularly cockroaches, such as *Blatella germanica, Blatta orientalis, Periplaneta americana*, mites, such as *Dermanyssus gallinae, Sarcoptes scabiei, Psoroptes ovis* and *Psorergates* spp. and last but not least ticks. The latter belong to the order Acarina. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

Ticks may be divided into hard and soft ticks, and are characterised by infesting one, two or three host animals. They attach themselves to a passing host animal and suck the blood or body fluids. Fully engorged female ticks drop from the host animal and lay large amounts of eggs (2000 to 3000) in a suitable crack in the floor or in any other protected site where the larvae hatch. These in turn seek a host animal, in order to suck blood from it. Larvae of ticks which only infest one host animal moult twice and thus become nymphs and finally adult ticks without leaving the host they have selected. Larvae of ticks which infest two or three host animals leave the animal after feeding on the blood, moult in the local environment and seek a second or third host as nymphs or as adult ticks, in order to suck its blood.

Ticks are responsible world-wide for the transmission and spread of many human and animal diseases. Because of their economic influence, the most important ticks are *Boophilus, Rhipicephalus, Ixodes, Hyalomma, Amblyomma* and *Dermacentor*. They are carriers of bacterial, viral, rickettsial and protozoal diseases and cause tick-paralysis and tick-toxicosis. Even a single tick can cause paralysis whereby its saliva penetrates into the host animal during ingestion. Diseases caused by ticks are usually transmitted by ticks which infest several host animals. Such diseases, for example babesiosis, anaplasmosis, theileriasis and heart water disease, are responsible for the death or impairment of a large number of domestic and farm animals in the entire world. In many countries of temperate climate, ixodide ticks transmit the agent of the chronically harmful Lyme's disease from wild animals to humans. Apart from the transmission of disease, the ticks are responsible for great economic losses in livestock production. Losses are not confined to the death of the host animals, but also include damage to the coats, loss of growth, a reduction in milk production and reduced value of the meat. Although the harmful effects of a tick infestation on animals have been known for years, and enormous progress has been made using tick-control programmes, until now no completely satisfactory methods of controlling or eliminating these parasites have been found, and in addition, ticks have often developed resistance to chemical active ingredients.

The infestation of fleas on domestic animals and pets likewise still represents for the owner a problem which has not been satisfactorily resolved or can only be resolved at considerable expense. As with ticks, fleas are not only troublesome, but are carriers of disease, and transmit various fungal diseases from host animal to host animal and to the animal keeper, particularly in moist, warm climatic areas, for example in the Mediterranean, in the southern part of USA, etc. Those at risk in particular are people with a weakened immune system or children whose immune system has not yet fully developed. Owing to their complex life cycle, none of the known methods for the control of fleas is completely satisfactory, especially as most known methods are basically directed towards the control of adult fleas in the coat, and leave completely untouched the different juvenile stages of the fleas, which exist not only in the coat of the animal, but also on the floor, in carpets, in the bedding of the animal, on chairs, in the garden and all other places with which the infested animal comes into contact. Flea treatment is usually expensive and has to be continued over long periods of time. Success usually depends on treating not only the infested animal, e.g. the dog or cat, but at the same time all the locations which the infested animal frequents.

Such a complicated procedure is unnecessary with the present compounds of formula (I), since a particular advantage of the compounds of formula (I) under discussion is that they are extremely effective and at the same time of very low toxicity both for the target parasites and for the warm-blooded animals. This is because their activity is based not on the death of the target parasite, but on the parrying defence thereof, before it attacks, stings, bites or in any other way harms the host organism. The presence of the compounds of formula (I) being discussed here appears to disturb the parasites in such a way that they suddenly leave the treated environment without biting or stinging, or even do not infest a treated host animal at all. What is striking is that the effect sets in when the parasite comes into contact with the active ingredient for a short time. After contact for a short time, the parasite avoids any further contact with the active ingredient. An additional advantage lies in the long-term action, e.g. compared with DEET (N,N-diethyl-m-toluamide), which although very effective, volatilizes rather rapidly and therefore has to be reapplied already after ca. 2 hours, and is thus not appropriate for the long-term treatment of animals Usage of the present active ingredients is also pleasant because they are almost odourless.

Although the present active ingredients can of course be mixed with other substances having the same sphere of activity or with parasiticides or with other activity-improving substances to achieve further improved or longer-lasting action, and then applied, in contrast to many compounds of the prior art, this is totally unnecessary, as they already combine all the advantageous properties.

If the parasite is not only to be kept at bay, but also killed, of course this can be achieved by adding appropriate insecticides and/or acaricides. In practice, however, this is unnecessary in most cases.

The compounds of formula (I) are conveniently applied in the form of diluted solutions to the coat of an animal or to the human skin; in addition, they can also be converted into other application forms and used in the form of pastes, sprays, or incorporated in collars or tags. These latter forms of application are of particular advantage if long-term efficacy is desired, since pastes, collars and tags are conceived in such a way that they can take up relatively large amounts of active ingredient and release it over longer periods. Such slow-release formulations have been known to the person skilled in the art for a long time.

To product collars, polyvinyl resins, polyurethanes, polyacrylates, epoxy resins, cellulose, cellulose derivatives, polyamides and polyesters are used in known manner, and these are sufficiently compatible with the above-mentioned active ingredients. The polymers should have sufficient strength and pliability so as not to tear or become brittle when shaped into a band. They must be sufficiently long-lasting so as to be resistant to normal wear and tear. In addition, the polymers must allow the active ingredients to migrate satisfactorily to the surface of the moulded collar. These requirements are fulfilled in particular by solid polyvinyl resins, i.e. polymerisation products formed by polymerisates of a vinyl double bond. Typical vinyl resins are, for example, polyvinyl halides, such as polyvinyl chloride, polyvinyl chloride-vinyl acetate and polyvinyl fluoride; polyacrylater and polymethacrylate esters, such as polymethyl acrylate and polymethyl methacrylate; and polyvinylbenzenes, such as polystyrene and polyvinyltoluene.

In order to produce collars based on polyvinyl resin, appropriate plasticizers are those that are usually used for plasticizing solid vinyl resins. Which plasticizer is to be used depends on the resin and its compatibility with the plasticizer. Suitable plasticizers are, for example, esters of phosphoric acid, such as tricresyl phosphate, esters of phthalic acid, such as dimethyl phthalate and dioctyl phthalate, and esters of adipic acid, such as diisobutyl adipate. Other esters may also be used, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidised soy bean oils. The amount of plasticizer is ca. 10 to 50% by weight, preferably 20 to 45% by weight, of the total composition.

The collars may also contain further constituents, such as stabilizers, disintegrants, lubricants, fillers and colourants, without changing the underlying properties of the composition. Suitable stabilizers are antioxidants and agents which protect the collars from ultraviolet radiation and undesired degradation during processing, such as extrusion. A few stabilizers, such as epoxidised soy bean oils, additionally serve as secondary plasticizers. The lubricants used may be, for example, stearates, stearic acid and polyethylenes of a low molecular weight. These constituents may be used in a concentration of up to 5% by weight of the total composition.

When producing collars based on vinyl, the different constituents are dry-mixed by known mixing processes, and produced by known extrusion methods.

The choice of processing method in the production of the collars according to the invention depends on a technical basis on the rheological properties of the collar material and the shape of the desired collar. The processing method may be adjusted according to the processing technology or according to the type of shaping. In the processing technology, the processes may be classified according to the continuous rheological conditions therein.

According to these, for viscous collar materials pouring, pressing, injecting and coating may be considered, and for elastoviscous polymers injection moulding, extrusion, calendering, rolling and optionally edging may be considered. When classified according to the type of shaping, the moulded collars according to the invention may be produced by pouring, immersion, pressing, injection-moulding, extrusion, calendering, stamping, bending, cupping, etc.

These processing methods are known and need no further explanation. In principle, the explanations given above by way of example for polyvinyl resins also apply to polymers such as polyamides and polyesters.

Further carrier materials for the collars according to the invention are polyurethanes. These are produced in known manner by reacting polyisocyanates with higher molecular compounds, which have at least two groups that are reactive towards isocyanates, as well as optionally with low molecular chain lengtheners and/or monofunctional chain terminators. The active ingredients are present in the carrier polymers in concentrations of 0.1-30% by weight. Concentrations of 10-20% by weight are preferred. A concentration of active ingredient of around 20% by weight is especially preferred.

The present active ingredients are preferably used in diluted form. Normally, they are brought to the final application form by using appropriate formulation excipients, and they then contain between 0.1 and 95% by weight, preferably 0.5 to 90% by weight of the active ingredient. Simple alcoholic solutions in lower alkanols, such as ethanol, propanol or isopropanol may be used with great success, without the need for further excipients. Simple solutions of this kind are preferred in particular in the scope of the present invention. Since the active ingredients are in many instances applied to warm-blooded animals and of course come into contact with the skin, suitable formulation excipients are also the excipients and administration forms that are known in cosmetics. They may be administered in the form of solutions, emulsions, ointments, creams, pastes, powders, sprays, etc. For administration to productive livestock or pets and stable animals, such as cows, horses, asses, camels, dogs, cats, poultry, sheep, goats, etc., the so-called 'pour-on' or 'spot-on' formulations are especially suitable; these liquid or semi-liquid formulations have the advantage that they only have to be applied to a small area of the coat or plumage, and, thanks to the proportion of spreading oils or other spreading additives, they disperse by themselves over the whole coat or plumage, without having to do anything else, and become active over the whole area.

Of course, inanimate materials, for example clothing or dog and cat baskets, stables, carpets, curtains, living quarters, conservatories, etc. may be treated with said formulations and thus protected from parasite infestation.

To control cockroaches, their locus, usually cracks in the walls, furniture, etc., can be sprayed or powdered. Since cockroaches are extremely vigorous and it is almost impossible to drive them away completely, it is recommended that when using the present active ingredients, insecticides having activity against cockroaches are used additionally.

For application on humans, a pleasant-smelling essence, e.g. a perfume, can be added to make application more attractive.

The following examples of preparation and usage of the active ingredients according to the invention serve to illustrate the invention without restricting it.

In particular, preferred formulations are made up as follows:

FORMULATION EXAMPLE 1

A vermin-deterring composition in the form of a lotion for application to the skin is prepared by mixing 30 parts of one of the compounds of formula (I) from Table 1, 1.5 parts of perfume and 68.5 parts of isopropanol, whereby the latter may be replaced by ethanol.

FORMULATION EXAMPLE 2

A vermin-deterring composition in the form of an aerosol for spraying onto the coat of a pet is prepared by formulating 50% active ingredient solution, consisting of 30 parts of one of the compounds of formula (I) from Table 1, 1.5 parts of perfume and 68.5 parts of isopropanol, with 50% Frigen 11/12 (a halogenated hydrocarbon) as propellant gas in an aerosol can.

FORMULATION EXAMPLE 3

A vermin-deterring composition in the form of an aerosol for spraying onto the skin is prepared by formulating 40% active ingredient solution, consisting of 20 parts of one of the compounds of formula (I), 1 part of perfume, 79 parts of isopropanol, with 60% propane/butane (in a ratio of 15:85) as propellant gas in an aerosol can.

PREPARATION EXAMPLE

Preparation of 2-propyl-pentanoic acid-bis-(2-methoxy-ethyl)-amide (compound no. 1.31 in the following table 1) having the formula below

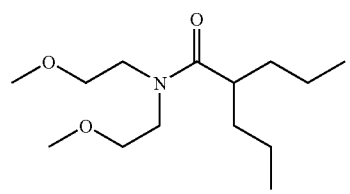

A solution of 162.5 g (0.50 mols) of 2-propyl-pentanoyl chloride in 300 ml of methylene chloride is added dropwise at 10° C. to a solution of 75 g (0.56 mols) of bis-(2-methoxy-ethyl)-amine and 50.6 g (0.50 mols) of triethylamine in 700 ml of methylene chloride. The reaction mixture is stirred for ca. 12 h at room temperature and then the reaction solution is washed with 250 ml each of $H_2O$, 1N NaOH, 1 N HCl and aqueous sodium chloride solution. Subsequently, the organic phase is separated and concentrated by evaporation, and the residue is distilled under a high vacuum (0.1 torr) over a Vigreux column (boiling temperature: 108-112° C.). 121 g (93%) of a colourless and odourless oil are obtained.

As already specified, the compounds of formula (I) are colourless to pale yellow, neutral-tasting oils, which are relatively readily volatile.

The following table 1 shows preferred representatives of compounds of formula (I).

TABLE 1

Compounds of formula (I)

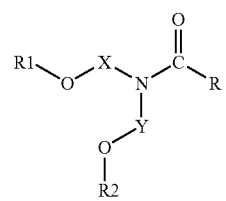

| No. | R | X | Y | R1 | R2 |
|---|---|---|---|---|---|
| 1.01 | $CH_3$ | $CH_2$ | $CH_2$ | $CH_3$ | $CH_3$ |
| 1.02 | $CH_3$ | $CH_2$ | $CH_2$ | $C_2H_5$ | $CH_3$ |
| 1.03 | $CH_3$ | $CH_2$ | $CH_2$ | $C_2H_5$ | $C_2H_5$ |
| 1.04 | $CH_3$ | $(CH_2)_2$ | $CH_2$ | $C_2H_5$ | $C_2H_5$ |
| 1.05 | $CH_3$ | $(CH_2)_2$ | $(CH_2)_2$ | $C_2H_5$ | $C_2H_5$ |
| 1.06 | $C_2H_5$ | $CH_2$ | $CH_2$ | $CH_3$ | $CH_3$ |
| 1.07 | $C_2H_5$ | $CH_2$ | $CH_2$ | $C_2H_5$ | $CH_3$ |
| 1.08 | $C_2H_5$ | $CH_2$ | $CH_2$ | $C_2H_5$ | $C_2H_5$ |
| 1.09 | $C_2H_5$ | $(CH_2)_2$ | $CH_2$ | $C_2H_5$ | $C_2H_5$ |
| 1.10 | $C_2H_5$ | $(CH_2)_2$ | $(CH_2)_2$ | $C_2H_5$ | $C_2H_5$ |
| 1.11 | $C_3H_7$-n | $CH_2$ | $CH_2$ | $CH_3$ | $CH_3$ |
| 1.12 | $C_3H_7$-n | $CH_2$ | $CH_2$ | $C_2H_5$ | $CH_3$ |
| 1.13 | $C_3H_7$-n | $CH_2$ | $CH_2$ | $C_2H_5$ | $C_2H_5$ |
| 1.14 | $C_3H_7$-n | $(CH_2)_2$ | $CH_2$ | $C_2H_5$ | $C_2H_5$ |
| 1.15 | $C_3H_7$-n | $(CH_2)_2$ | $(CH_2)_2$ | $C_2H_5$ | $C_2H_5$ |
| 1.16 | $C_3H_7$-i | $CH_2$ | $CH_2$ | $CH_3$ | $CH_3$ |
| 1.17 | $C_3H_7$-i | $CH_2$ | $CH_2$ | $C_2H_5$ | $CH_3$ |
| 1.18 | $C_3H_7$-i | $CH_2$ | $CH_2$ | $C_2H_5$ | $C_2H_5$ |
| 1.19 | $C_3H_7$-i | $(CH_2)_2$ | $CH_2$ | $C_2H_5$ | $C_2H_5$ |
| 1.20 | $C_3H_7$-i | $(CH_2)_2$ | $(CH_2)_2$ | $C_2H_5$ | $C_2H_5$ |
| 1.21 | $CH(C_2H_5)_2$ | $CH_2$ | $CH_2$ | $CH_3$ | $CH_3$ |
| 1.22 | $CH(C_2H_5)_2$ | $CH_2$ | $CH_2$ | $C_2H_5$ | $CH_3$ |
| 1.23 | $CH(C_2H_5)_2$ | $CH_2$ | $CH_2$ | $C_2H_5$ | $C_2H_5$ |
| 1.24 | $CH(C_2H_5)_2$ | $(CH_2)_2$ | $CH_2$ | $C_2H_5$ | $C_2H_5$ |
| 1.25 | $CH(C_2H_5)_2$ | $(CH_2)_2$ | $(CH_2)_2$ | $C_2H_5$ | $C_2H_5$ |
| 1.26 | $CH(C_2H_5)(C_3H_7$-n$)$ | $CH_2$ | $CH_2$ | $CH_3$ | $CH_3$ |
| 1.27 | $CH(C_2H_5)(C_3H_7$-n$)$ | $CH_2$ | $CH_2$ | $C_2H_5$ | $CH_3$ |
| 1.28 | $CH(C_2H_5)(C_3H_7$-n$)$ | $CH_2$ | $CH_2$ | $C_2H_5$ | $C_2H_5$ |
| 1.29 | $CH(C_2H_5)(C_3H_7$-n$)$ | $(CH_2)_2$ | $CH_2$ | $C_2H_5$ | $C_2H_5$ |
| 1.30 | $CH(C_2H_5)(C_3H_7$-n$)$ | $(CH_2)_2$ | $(CH_2)_2$ | $C_2H_5$ | $C_2H_5$ |
| 1.31 | $CH(C_3H_7$-n$)_2$ | $CH_2$ | $CH_2$ | $CH_3$ | $CH_3$ |
| 1.32 | $CH(C_3H_7$-n$)_2$ | $CH_2$ | $CH_2$ | $C_2H_5$ | $CH_3$ |
| 1.33 | $CH(C_3H_7$-n$)_2$ | $CH_2$ | $CH_2$ | $C_2H_5$ | $C_2H_5$ |
| 1.34 | $CH(C_3H_7$-n$)_2$ | $(CH_2)_2$ | $CH_2$ | $C_2H_5$ | $C_2H_5$ |
| 1.35 | $CH(C_3H_7$-n$)_2$ | $(CH_2)_2$ | $(CH_2)_2$ | $C_2H_5$ | $C_2H_5$ |
| 1.36 | $CH(C_3H_7$-n$)(C_4H_9$-n$)$ | $CH_2$ | $CH_2$ | $CH_3$ | $CH_3$ |
| 1.37 | $CH(C_3H_7$-n$)(C_4H_9$-n$)$ | $CH_2$ | $CH_2$ | $C_2H_5$ | $CH_3$ |
| 1.38 | $CH(C_3H_7$-n$)(C_4H_9$-n$)$ | $CH_2$ | $CH_2$ | $C_2H_5$ | $C_2H_5$ |
| 1.39 | $CH(C_3H_7$-n$)(C_4H_9$-n$)$ | $(CH_2)_2$ | $CH_2$ | $C_2H_5$ | $C_2H_5$ |
| 1.40 | $CH(C_3H_7$-n$)(C_4H_9$-n$)$ | $(CH_2)_2$ | $(CH_2)_2$ | $C_2H_5$ | $C_2H_5$ |
| 1.41 | $CH(C_4H_9$-n$)_2$ | $CH_2$ | $CH_2$ | $CH_3$ | $CH_3$ |
| 1.42 | $CH(C_4H_9$-n$)_2$ | $CH_2$ | $CH_2$ | $C_2H_5$ | $CH_3$ |
| 1.43 | $CH(C_4H_9$-n$)_2$ | $CH_2$ | $CH_2$ | $C_2H_5$ | $C_2H_5$ |

TABLE 1-continued

Compounds of formula (I)

$$R1\!-\!O\!-\!X\!-\!N(Y\!-\!O\!-\!R2)\!-\!C(=\!O)\!-\!R$$

| No. | R | X | Y | R1 | R2 |
|---|---|---|---|---|---|
| 1.44 | $CH(C_4H_9\text{-}n)_2$ | $(CH_2)_2$ | $CH_2$ | $C_2H_5$ | $C_2H_5$ |
| 1.45 | $CH(C_4H_9\text{-}n)_2$ | $(CH_2)_2$ | $(CH_2)_2$ | $C_2H_5$ | $C_2H_5$ |
| 1.46 | $CH(C_5H_{11}\text{-}n)_2$ | $CH_2$ | $CH_2$ | $CH_3$ | $CH_3$ |
| 1.47 | $CH(C_5H_{11}\text{-}n)_2$ | $CH_2$ | $CH_2$ | $C_2H_5$ | $CH_3$ |
| 1.48 | $CH(C_5H_{11}\text{-}n)_2$ | $CH_2$ | $CH_2$ | $C_2H_5$ | $C_2H_5$ |
| 1.49 | $CH(C_5H_{11}\text{-}n)_2$ | $(CH_2)_2$ | $CH_2$ | $C_2H_5$ | $C_2H_5$ |
| 1.50 | $CH(C_5H_{11}\text{-}n)_2$ | $(CH_2)_2$ | $(CH_2)_2$ | $C_2H_5$ | $C_2H_5$ |
| 1.51 | $CH(C_6H_{13}\text{-}n)_2$ | $(CH_2)_2$ | $(CH_2)_2$ | $C_2H_5$ | $C_2H_5$ |
| 1.52 | $CH(C_6H_{13}\text{-}n)_2$ | $CH_2$ | $CH_2$ | $CH_3$ | $CH_3$ |
| 1.53 | $CH(C_6H_{13}\text{-}n)_2$ | $CH_2$ | $CH_2$ | $C_2H_5$ | $CH_3$ |
| 1.54 | $CH(C_6H_{13}\text{-}n)_2$ | $CH_2$ | $CH_2$ | $C_2H_5$ | $C_2H_5$ |
| 1.55 | $CH(C_6H_{13}\text{-}n)_2$ | $(CH_2)_2$ | $CH_2$ | $C_2H_5$ | $C_2H_5$ |

BIOLOGICAL EXAMPLES

Arena Test Method for Testing Vermin-repellent Substances

This method is carried out in titre plates having 6 wells with a cross-section of 5 cm each, using a computer-supported video system. Each well of the titre plate is lined with a circular filter paper or another suitable carrier material. The substance of formula (I) to be tested is dissolved in methanol, acetonitrile or another suitable solvent, with ultrasound treatment and heating being employed for poorly-soluble substances. In an amount of 1 to 100 µg/cm$^2$, the dissolved test substance is placed in the centre of the filter paper on a quadrant or circular area of ca. 2.4 cm$^2$ radius. 4 of the 6 wells are filled with different test substances or with the same test substance in different dilutions (e.g. 1, 3.2, 5, 10 and 20 µg/cm$^2$) The 5th well is treated with DEET (N,N-diethyl-m-toluamide) as standard substance. The 6th well is filled with the pure solvent and serves as a control. 60 to 100 larvae or 25 to 50 nymphs or 10 to 25 adults of the parasite to be tested, e.g. ticks, are added to each filter paper, and the system is covered with a pane of glass and positioned under a video camera.

At intervals of 5 seconds, the video camera takes individual pictures of all 6 wells. For a qualitative evaluation, these images are observed in a time-lapse as a continuous film, optically following the movements of the parasites on the filter paper and comparing them with the movements in the control well no. 6 or with the standard in the 5th well. A qualitative observation is thus made as to whether the test parasites move evenly over the whole surface of the filter paper and ignore the test substance, or whether and over what period they avoid the treated zone, and what influence the dilution of the test substance has on the behaviour of the test parasites. In this way, neutral and repellent substances are determined. At the same time, the duration of activity of the test substance is determined and compared with that of the standard. By plotting all the images for each individual well over one another, different areas of density are obtained. This represents the frequency at which the parasites visit certain places. This frequency is evaluated statistically and thus quantitatively by the Willcoxon method in a comparison with the control and with the standard. Compounds from table 1, such as nos. 1.11 to 1.31, 1.45, 1.47 and 1.55, show outstanding activity. Compound no. 1.31 has proved to be particularly active.

Arena Test in vitro Against *Amblyomma hebraeum* or *variegatum* (Nymphs)

The test is carried out as described above, with ca. 25 to 50 nymphs being added per well. 10 mg of dissolved test substance is applied to an area of 2.4 cm$^2$ radius. An evaluation of the video images shows that the compounds of formula (I) display marked repellent action against *Amblyomma* nymphs, which lasts considerably longer than that of DEET. An especially marked long-term action is shown e.g. by compound no. 1.31 even up to a dilution of 3.2 µg/cm$^2$.

Arena Test in vitro Against *Boophilus microplus Biarra* (Larvae)

The test is carried out as described above, with ca. 60 to 100 larvae being added per well. 10 mg of dissolved test substance is applied to an area of 2.4 cm$^2$ radius. An evaluation of the video images shows that the compounds of formula (I) display marked repellent action against *Bophilus* larvae, which lasts considerably longer than that of DEET. An especially marked long-term action is shown e.g. by compound no. 1.31 even up to a dilution of 3.2 µg/cm$^2$.

Arena Test in vitro Against *Rhipicephalus sanguineus* (Nymphs)

A test is carried out analogously to example B using ca. 40 to 50 nymphs. An evaluation of the video images shows that the compounds according to the invention display good repellent action. In particular, the compounds are notable for their almost complete repellent action, which lasts considerably longer than that of DEET. An especially marked long-term action is shown e.g. by compound no. 1.31 even up to a dilution of 3.2 µg/cm$^2$.

In analogous test set-ups, the same test substances are tested for their attractant activity to various species of fly, such as *Musca domestica*. It is shown that the substances mentioned above display strong repellent action even with these tested models.

In-vivo comparison on dogs in respect of the anti-tick action of 2-propyl-pentanoic acid-bis-(2-methoxyethyl)-amide according to the present invention with DEET (in the form of PARAPIC DOG® (a tick repellent containing DEET)) following spray application.

The following formulations of active ingredient are used in the test which follows:

Prior art composition of the Parapic anti-tick spray:
active substance: 15% N,N-Diethyl-3-methylbenzamide (DEET); 15%
ethylbutylacetylaminopropionate (EBMP), isopropanol, methacrylic acid copolymer, carbamide, fragrance (perfume).

Inventive composition of the 2-propyl-pentanoic acid-bis-(2-methoxyethyl )-amide spray: active substance: 2-propyl-pentanoic acid-bis-(2-methoxyethyl )-amide 4.5%; Pluronic F6® 2.0%; water 10.0%, isopropanol ad 100.0%.

Pluronic® is a non-ionic surface-active substance (surfactant) consisting of the block copolymers of propylene oxide and ethylene oxide.

The aim of the test is to make a comparison, under natural conditions, of the commercially available anti-vermin product Parapic Dog® with a typical representative of a compound of formula (I), namely 2-propyl-pentanoic acid-bis-(2-methoxyethyl)-amide. According to the packaging information one should reach with Parapic Dog® an 80% anti-tick protection over a period of 48 hours. The active ingredient of Parapic Dog® is DEET, which is the chemical substance N,N-Diethyl-3-methylbenzamide. Products based on the active ingredient DEET, such as Parapic Dog® are widely used against ticks on dogs and cats, and also on humans. Actually, the majority of the currently used anti-tick products is based on DEET, and the mostly used product in dogs is said Parapic Dog®.

Test Protocol: 12 Beagle dogs are divided into groups of 4. To distinguish them, each dog is given a numbered label. Group 1 is treated with a 4.5% 2-propyl-pentanoic acid-bis-(2-methoxy-ethyl)-amide spray (3645mg a.i./m$^2$). Group 2 is treated with Parapic Dog®-Spray (20% DEET/3645 mg a.i./m$^2$). Group 3 remains untreated and serves as a control.

All twelve dogs are taken on 3 successive days to a wooded plot infected with ticks of the genus *Ixodes ricinus* and are left to run around there. They are free to move around there for 2 hours. An evaluation is made directly after returning from the wood. The two-hour walks are repeated on the next 2 days without the dogs being treated again, and the evaluation is again made directly after returning from the wood. This is effected by carefully searching the fur and the skin of each animal for ticks adhered thereto. The ticks are counted and compared with the number of ticks in the control group. No skin irritation or other undesired side effects were noted in any of the dogs.

The test leads to the following results:

| substance | anti-tick action | | |
|---|---|---|---|
| | after 1 day | after 2 days | after 3 days |
| Parapic | 98% | 70% | — |
| 2-propyl-pentanoic acid-bis-(2-methoxyethyl)-amide | 100% | 98% | 79% |

The comparison shows that the substance 2-propyl-pentanoic acid-bis-(2-methoxy-ethyl)-amide according to the present invention is vastly superior to DEET which is used most frequently at the present time. 2-propyl-pentanoic acid-bis-(2-methoxy-ethyl)-amide according to the present invention leads in the course of 3 successive days to very good results, while the activity of DEET drops abruptly after 2 days.

The compounds of formula (I) according to the invention are consequently suitable for the production of a product which, after a single application, gives protection against ticks for a whole weekend without showing any undesirable side effects. The compounds are well tolerated by animals and humans. No irritations or other negative effects have been observed.

What is claimed is:

1. A compound of formula (I)

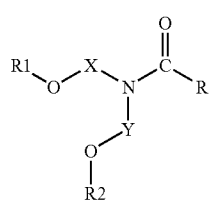

(I)

wherein

R1 and R2 are unbranched or branched $C_1$-$C_{12}$ alkyl, which is unsubstituted or substituted by halogen, cyano or nitro; and X and Y, independently of one another, are a straight-chain or branched alkylene bridge with 1 to 20 carbon atoms, which is unsubstituted or substituted by halogen, cyano or nitro; and R is $CH(C_2$-$C_4$ alkyl$)_2$, whereby the two $C_2$-$C_4$ alkyl radicals are identical and unbranched.

2. The compound of formula (I) according to claim 1, wherein R is $CH(n$-$C_3H_7)_2$.

3. The compound of formula (I) according to claim 1 wherein said compound is 2-propyl-pentanoic acid-bis-(2-methoxyethyl)-amide.

4. A vermin-repellent composition comprising a compound of formula (I) according to claim 1, and at least one diluent or a spreading additive.

5. The vermin-repellent composition according to claim 4, wherein R is $CH(n$-$C_3H_7)_2$.

6. The vermin-repellent composition according to claim 4, wherein X and Y, independently of one another, are methylene or ethylene.

7. The vermin-repellent composition according to claim 4, wherein R1 and R2, independently of one another, are methyl or ethyl.

8. The vermin-repellent composition according to claim 4, wherein the compound of formula (I) is the compound 2-propyl-pentanoic acid-bis-(2-methoxy-ethyl)-amide.

9. The vermin-repellent composition according to claim 4, whereby said composition is in the form of an alcoholic solution.

10. The vermin-repellent composition according to claim 4, whereby said composition is in a pour-on or spot-on formulation.

11. The vermin-repellent composition according to claim 4, whereby said composition is in the form of a collar or tag.

12. A method for deterring vermin from an animal, a human, or an object comprising applying to said animal, human, or object, an amount of the compound of claim 1 which deters said vermin.

13. A method for repelling vermin from an animal, a human, or an object comprising applying to said animal, human, or object, an amount of the compound of claim 1 which repels said vermin.

14. A method for deterring vermin from an animal, a human or an object comprising applying to said animal, human, or object, an amount of a vermin-deterrent composition comprising a compound of formula (I)

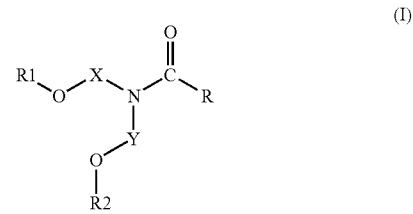

(I)

wherein

R is unbranched or branched $C_1$-$C_{15}$ alkyl, which is unsubstituted or substituted by halogen, cyano or nitro;

each of R1 and R2 individually is unbranched or branched $C_1$-$C_{12}$ alkyl, which is unsubstituted or substituted by halogen, cyano or nitro;

each of X and Y, independently of one another, is a straight-chain or branched alkylene bridge with 1 to 20 carbon atoms, which is unsubstituted or substituted by halogen, cyano or nitro; and at least one diluent or a spreading additive, which deters said vermin.

15. A method for repelling vermin from an animal, a human or an object comprising applying to said animal, human, or object, an amount of a vermin-repellent composition comprising a compound of formula (I)

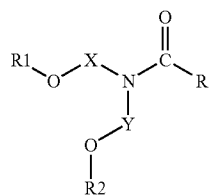

(I)

wherein

R is unbranched or branched $C_1$-$C_{15}$ alkyl, which is unsubstituted or substituted by halogen, cyano or nitro;

each of R1 and R2 individually is unbranched or branched $C_1$-$C_{12}$ alkyl, which is unsubstituted or substituted by halogen, cyano or nitro;

each of X and Y, independently of one another, is a straight-chain or branched alkylene bridge with 1 to 20 carbon atoms, which is unsubstituted or substituted by halogen, cyano or nitro; and at least one diluent or a spreading additive, which repels said vermin.

* * * * *